United States Patent [19]

Cassidy et al.

[11] 4,294,972

[45] Oct. 13, 1981

[54] 1,2-DISUBSTITUTED OXO TRIAZOLIDINE

[75] Inventors: Frederick Cassidy; Alexander C. Goudie, both of Harlow, England

[73] Assignee: Beecham Group Limited, England

[21] Appl. No.: 48,390

[22] Filed: Jun. 14, 1979

[30] Foreign Application Priority Data

Jun. 15, 1978 [GB] United Kingdom ............... 27060/78

[51] Int. Cl.$^3$ ..................... A61K 31/41; C07D 249/12
[52] U.S. Cl. .................................... 548/264; 424/269;
260/456 P; 260/465.6; 560/29; 560/159;
560/160; 568/415; 568/417; 568/419; 564/18;
564/34; 564/503
[58] Field of Search ........................ 548/264; 424/269

[56] References Cited

U.S. PATENT DOCUMENTS

| | | | |
|---|---|---|---|
| 2,944,060 | 7/1960 | Close et al. ........................ | 548/264 |
| 4,032,533 | 6/1977 | Scribner ............................. | 424/270 |
| 4,052,407 | 10/1977 | Ambrus et al. .................... | 424/270 |
| 4,079,145 | 3/1978 | Reuschling et al. ................ | 424/274 |

FOREIGN PATENT DOCUMENTS 1135 7/1977 Ireland ............................... 548/264

*Primary Examiner*—Alton D. Rollins
*Attorney, Agent, or Firm*—Jacobs & Jacobs

[57] ABSTRACT

Compounds of the formula (I):

$$\underset{R_5-N\underset{\underset{O}{\|}}{\diagdown}N\diagdown}{L\diagup\diagup N\diagdown}\overset{\displaystyle CH_2-Y-(CH_2)_n-\overset{\overset{\displaystyle O}{\|}}{C}-R_1}{\underset{\displaystyle N\diagdown\underset{R_3}{\diagup}\underset{R_4}{\diagdown}R_2}{}} \quad (I)$$

wherein
n is 3 to 5;
Y is —CH$_2$—CH$_2$, —CH=CH— or C≡C—;
L is O or S;
R$_1$ is C$_{1-4}$ alkyl;
R$_2$ is hydrogen, C$_{1-4}$ alkyl or phenyl;
R$_3$ is hydroxy or protected hydroxy;
R$_4$ is hydrogen, C$_{1-9}$ alkyl, C$_{3-8}$ cycloalkyl, phenyl, naphthyl, any of which phenyl moieties or naphthyl moieties may be substituted by one or more halogen, trifluoromethyl, C$_{1-6}$ alkyl, hydroxy, C$_{1-6}$ alkoxy, phenyl C$_{1-6}$ alkoxy or nitro groups; or
R$_2$ and R$_4$ taken with the carbon atom to which they are joined represent a C$_{5-8}$ cycloalkyl group; and
R$_5$ is C$_{1-6}$ alkyl, having similar activity to natural prostaglandins, a process for their preparation, intermediates useful in that process and pharmaceutical compositions containing them.

14 Claims, No Drawings

1,2-DISUBSTITUTED OXO TRIAZOLIDINE

This invention relates to novel compounds having pharmacological activity, to a process for their preparation, to intermediates useful in that process and to pharmaceutical composition containing them.

Offenlegungsschrift No. 2,323,193 discloses that pyrazolidine derivatives of the formula (I)':

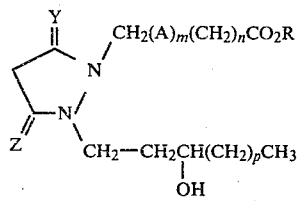

wherein:
A is CH=CH or C≡C; R is H, an alkali metal, an amine salt, or a ≯12 C hydrocarbon or chlorohydrocarbon residue; m is 0 or 1; n is 0-6; p is 0-6; and Y and Z are O or H except that Y and Z are not both 0; have similar biological properties to the prostaglandins or are antagonists of prostaglandins.

French Patent Application No. 2,258,376 discloses that 10-aza prostaglandins of formula (II)":

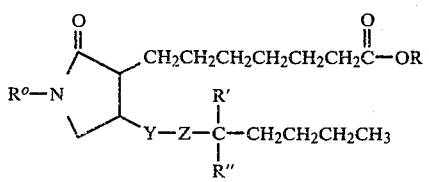

wherein:
R=H or lower alkyl; R' and R"=CH₃ or C₂H₅; R°=H or lower alkyl; Y=—CH₂—CH₂—, or —CH=CH—; Z=—CO or —CH(~OH)—; are useful in the treatment of blood pressure and gastro-intestinal disorders, and in the preparation for confinement.

Belgian Pat. No. 835989 discloses that compounds of the formula (III)":

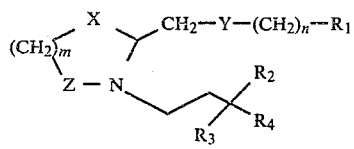

wherein:
X is CO, protected CO, CROH in which R is hydrogen or $C_{1-4}$ alkyl and in which the OH moiety may be protected; Y is CH₂CH₂ or CH=CH; Z is CO or CH₂; n is 1 to 8; m is 1, 2 or 3; R₁ is hydrogen, CH₂OH, CH₂OH in which the OH moiety is protected, CO₂W wherein W is hydrogen or CO₂W represents an ester group in which the ester moiety contains from 1 to 12 carbon atoms, or CONH₂; R₂ is hydrogen, $C_{1-4}$ alkyl, or taken together with R₃ and the carbon atom to which it is attached represents a carbonyl group; R₃ is hydrogen, hydroxy or protected hydroxy; R₄ is hydrogen or $C_{1-9}$ alkyl; and salts thereof; have useful pharmacological activity.

A novel class of compounds also having useful pharmacological activity has now been discovered, which compounds are structurally distinct from the prior art referred to above.

Accordingly the present invention provides a compound of the formula (I):

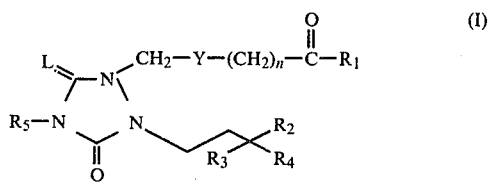

wherein:
n is 3 to 5;
Y is —CH₂—CH₂, —CH=CH— or C≡C—; L is O or S;
R₁ is $C_{1-4}$ alkyl;
R₂ is hydrogen, $C_{1-4}$ alkyl or phenyl;
R₃ is hydroxy or protected hydroxy;
R₄ is hydrogen, $C_{1-9}$ alkyl, $C_{3-8}$ cycloalkyl, phenyl, naphthyl, any of which phenyl moieties or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups; or
R₂ and R₄ taken with the carbon atom to which they are joined represent a $C_{5-8}$ cycloalkyl group; and
R₅ is $C_{1-6}$ alkyl.

Preferably n is 4.

Suitable examples of R₁ include methyl, ethyl, n- and iso propyl, and n-, sec- and tert-butyl. R₁ is preferably methyl.

Suitable examples of R₂ include hydrogen, methyl, ethyl, and phenyl. Preferred examples of R₂ include methyl.

Suitable protected hydroxy groups R₃ include readily hydrolysable derivatives such as acylated hydroxy groups in which the acyl moiety contains 1 to 4 carbon atoms, for example the acetoxy group; and hydroxy groups etherified by inert groups such as benzyl or methyl. Preferably however R₃ is hydroxy.

Suitable groups R₄ when R₄ is an alkyl group include $C_{4-9}$ alkyl groups. Such $C_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example, R₄ may be a group CH₂R₆, CH(CH₃)R₆ and C(CH₃)₂R₆ wherein R₆ is a straight chain alkyl group such that the carbon content of the resultant group R₄ is 4 to 9.

In general preferred groups R₄ when R₄ is an alkyl group include straight chain pentyl, hexyl and heptyl groups. Other preferred groups R₄ include groups CH(CH₃)R₆ C(CH₃)₂R₆ wherein R₆ is straight chain butyl, pentyl and hexyl.

When R₄ is a $C_{3-8}$ cycloalkyl moiety, the moiety may suitably be a $C_{5-8}$ cycloalkyl moiety such as a cyclohexyl moiety. It may also be a cyclopropyl moiety.

When R₂ and R₄ together with the carbon atom to which they are joined represent a $C_{5-8}$ cycloalkyl group, they suitably represent cyclohexyl.

When R₄ is an aryl group as previously defined, suitable groups R₄ include phenyl and naphthyl which groups may be substituted by normally one, two or three groups selected from those substituent groups listed hereinbefore. Examples of suitable substituent groups include fluorine, chlorine and bromine atoms and $CF_3$, methyl, ethyl, n- and iso-propyl, methoxy, ethoxy, n- and iso-propoxy and nitro groups. Other examples of such groups include hydroxy and benzyloxy. Preferably the aryl moieties when substituted by such groups will be mono- or disubstituted.

Suitable examples of $R_5$ include methyl, ethyl, n- and iso-propyl and n-butyl and such groups branched in the alkyl moiety by one or two methyl groups (at the same or different carbon atoms). Preferred $R_5$ groups include methyl.

A group of compounds within formula (I) is those wherein L is O, Y is —$CH_2$—$CH_2$— or —CH=CH—, and the remaining variables are as defined in formula (I).

One particularly suitable sub-group of compounds within formula (I) is of formula (II):

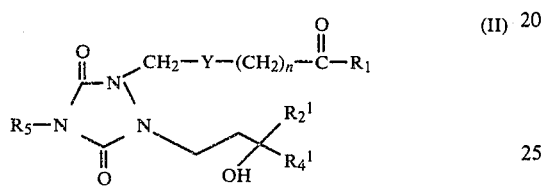

wherein:
Y, n, $R_1$ and $R_5$ are as defined in formula (I);
$R_2^1$ is hydrogen, methyl, ethyl or phenyl; and
$R_4^1$ is hydrogen or $C_{1-9}$ alkyl;
Suitably in formula (II) n is 4;
Suitably Y is —$CH_2CH_2$—;
Suitable $R_1$ are as listed as suitable under formula (I);
Suitably $R_2^1$ is hydrogen, methyl or ethyl.

While $R_4$ may be hydrogen or a $C_{1-9}$ alkyl group in formula (II), it is normally a $C_{4-9}$ alkyl group. In such cases suitable and preferred straight chain and branched groups $R_4^1$ include those previously described as suitable and preferred for the group $R_4$ when $R_4$ is a $C_{4-9}$ alkyl group. Such preferred groups $R_4^1$ include straight chain pentyl, hexyl and heptyl. Other preferred groups $R_4^1$ include $CH(CH_3)R_6^1$ and $C(CH_3)_2R_6^1$ wherein $R_6^1$ is straight chain butyl, pentyl or hexyl.

Preferably $R_5$ is methyl or ethyl, in particular methyl.

From the aforesaid it will be realised that one preferred group within formula (II) is of formula (III):

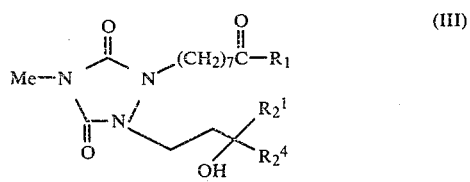

wherein:
$R_1$ is as defined in formula (I);
$R_2^1$ is hydrogen, methyl or ethyl; and
$R_4^2$ is a $C_{4-9}$ alkyl group;
Suitable $R_1$ are as listed as suitable under formula (I).
Suitable and preferred groups $R_4^2$ include those listed hereinbefore for $R_4^1$ when $R_4^1$ is a $C_{4-9}$ alkyl group.

Another particularly suitable sub-group of compounds within formula (I) is of formula (IV):

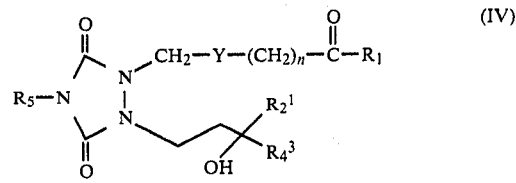

wherein:
Y, n, $R_1$, and $R_5$ are as defined in formula (I);
$R_2^1$ is hydrogen, methyl, ethyl or phenyl; and
$R_4^3$ is a group of formula (V):

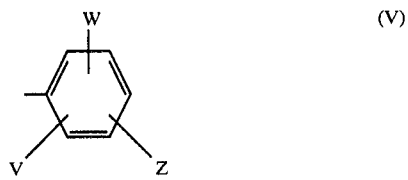

wherein:
V, W and Z are each hydrogen or fluorine, chlorine or bromine atoms, or $CF_3$, methyl, ethyl, n- or iso-propyl, methoxy, ethoxy, n or iso-propoxy or nitro groups.

In formula (IV) it is preferred that n is 4. Suitable $R_1$ are as listed as suitable under formula (I). In formula (V) V and W will often be hydrogen.

Often in formula (II) $R_5$ will be methyl or ethyl, preferably methyl.

A further sub-group of compounds within the formula (I) is of formula (VI):

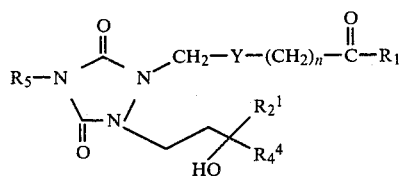

wherein the variable groups are as defined in formula (II) and $R_4^4$ is a group of formula (VII):

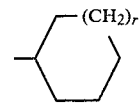

wherein r is 0-3, suitably 1.

Suitable and preferred variable groups in formula (VI) are so described under formula (II).

Another sub-group of compounds within formula (I) is of formula (VIII)

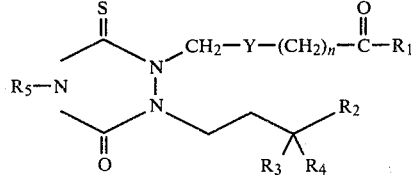

wherein the variables groups are as defined in formula (I).

Suitable and preferred variable groups in formula (VIII) are as so described under formula (I).

Process Variant (a)

The invention also provides a process for the preparation of a compound of the formula (I), which process comprises reacting a compound of formula (IX):

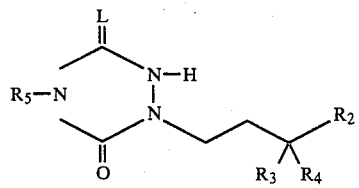

(IX)

wherein L, $R_2$, $R_3$, $R_4$, and $R_5$ are as defined in formula (I) with a compound of formula (X):

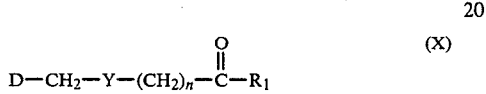

(X)

wherein D is a good leaving group and Y, n and $R_1$ are as defined in formula (I).

The reaction is suitably carried out in an inert solvent, such as hexamethylphosphormide or N,N-dimethylformamide, at room temperature, in the presence of a base such as lithium carbonate.

Suitable examples of D include mesylate and bromide.

Process Variant (b)

The invention also provides a process for the preparation of a compound of the formula (I) wherein L is O, which process comprises reacting a compound of formula (XI):

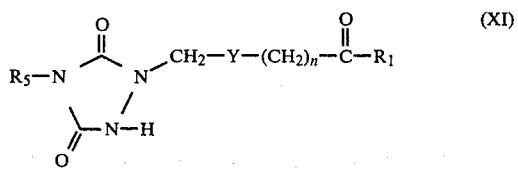

(XI)

wherein:
Y, n, $R_1$ and $R_5$ are as defined in formula (I), with a compound of formula (XII):

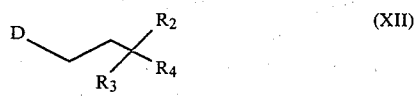

(XII)

wherein D is a good leaving group, and $R_2$, $R_3$ and $R_4$ are as defined in formula (I).

This reaction is suitably carried out in an inert organic solvent, such as hexamethylphosphoramide or N,N-dimethylformamide, at room temperature, in the presence of a base, such as sodium carbonate or sodium hydride, and a source of halide ions, such as an alkali metal halide. Suitable alkali halides include sodium iodide and lithium iodide.

Suitable examples of D include tosylate, bromide and iodide. Preferably D is a tosylate residue.

The groups $R_3$ and Y in the compounds of formula (I) may be varied by any conventional reaction which does not affect the oxo function.

Thus for example $R_3$ hydroxy may be acylated, alkylated or benzylated or de-acylated or de-alkylated.

Similarly, compounds of the formula (I) wherein Y is a —C≡C— or —CH=CH— group may be converted to their corresponding cis-—CH=CH— or —CH$_2$—CH$_2$ analogues by any of the usual reduction methods, which do not affect oxo functions, such as pallacdium-catalysed hydrogenation.

The preparation of the intermediates for use in the processes of the invention will now be described.

Process Variant (a), Intermediates

The compound of formula (IX) may be prepared by cyclising a compound of the formula (XIII):

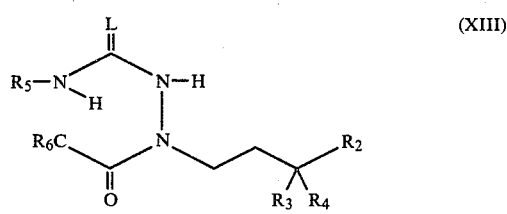

(XIII)

wherein L, $R_2$, $R_3$, $R_4$ and $R_5$ are as defined in formula (I) and $R_6$ is an organic group of up to 12 carbon atoms. Suitable groups $R_6$ include $C_{1-4}$ alkyl.

This reaction is suitably carried out in an inert organic solvent, such as benzene, at room temperature in the presence of a strong organic base, such as an alkali metal alkoxide, for example potassium tert-butoxide, or a polycyclic aza-substituted base such as DBU (diazabicycloundecene).

The compound of formula (XIII) is conveniently prepared, and subsequently cyclised in situ, by the reaction of a compound of formula (XIV):

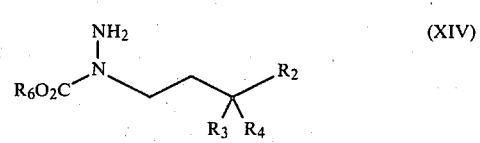

(XIV)

with a compound $R_5NCL$.

This reaction is conveniently carried out in an inert organic solvent, such as toluene, under reflux.

The compound of formula (XIV) may be prepared by the N-nitrosylation and reduction of a compound of the formula (XV):

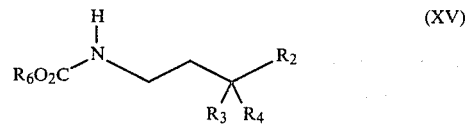

(XV)

in conventional manner, for example, by nitrosylation with aqueous $NaNO_2$/conc. $HNO_3$ at 0° C., and reduction of the product with zinc in glacial acetic acid/acetic anhydride in the presence of sodium acetate.

One suitable reaction scheme for the preparation of compounds of the formula (XV) is shown below:

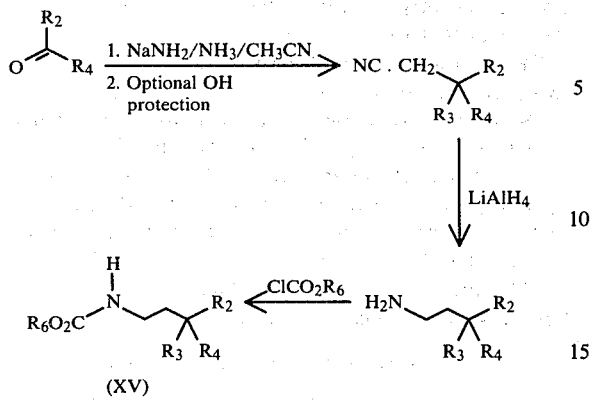

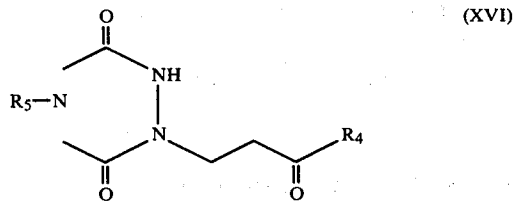
(XV)

The compound of formula (IX) wherein L is O may also be prepared by reacting a compound of the formula (XVI)

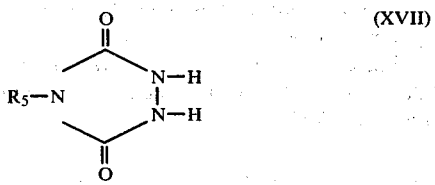
(XVI)

with a reducing agent to give a corresponding compound of formula (IX) wherein $R_2$ is hydrogen and $R_3$ is hydroxy, or with a $C_{1-4}$ alkyl or phenyl Grignard reagent or $C_{1-4}$ alkyl or phenyl metallic complex (Suitably $C_{1-4}$ alkyl or phenyl lithium) to give a corresponding compound of formula (IX) wherein $R_2$ is $C_{1-4}$ alkyl or phenyl, and $R_3$ is hydroxy.

Reduction may be carried out conventionally for example with sodium borohydride.

The reaction with organometallic reagents may be carried out under conventional conditions therefor, for example in an inert anhydrous aprotic solvent.

The $R_3$ hydroxy moiety so generated may optionally be protected in conventional manner, for example by acylating, alkylating or benzylating.

Compounds of the formula (XVI) may be prepared by reacting a compound of formula (VIII)

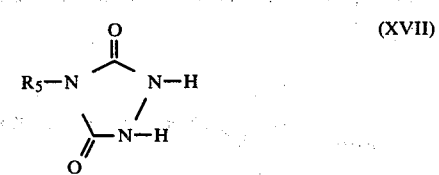
(XVII)

with a strong base and a compound of the formula (XVIII):

(XVIII)

Compounds of the formula (XVIII) are either known compounds or can be prepared in analogous manner to known compounds.

One suitable reaction scheme for the preparation of these compounds is shown below under 'Process Variant (b), Intermediates'.

Process Variant (b), Intermediates

The compound of formula (XI) wherein L is O and Y is trans —CH═CH— or —CH$_2$CH$_2$— may be prepared by reacting a compound of formula (XIX)

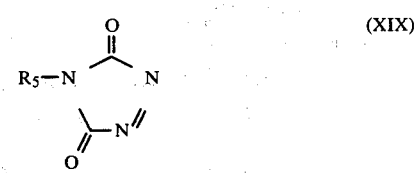
(XIX)

with a compound of formula

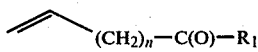

and if necessary reducing the resulting Y is CH═CH compound to the corresponding Y is CH$_2$CH$_2$ compound.

This reaction is suitably carried out in an inert organic solvent, such as benzene, at the reflux temperature, under an inert atmosphere.

The optional reduction can be carried out in conventional manner, e.g. by hydrogenation as above.

The compound of formula (XIX) may be prepared by treating a compound of formula (XVII)

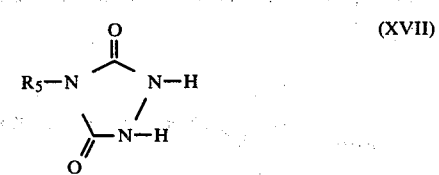
(XVII)

with an oxidizing agent, such as $N_2O_4$ or t-butyl hypochlorite.

This reaction is suitably carried out by suspending the chosen compound of the formula (XVII) in an inert organic solvent, such as dichloromethane, at 0° C., and bubbling $N_2O_4$ through this suspension, or adding a known volume of $N_2O_4$ in dichloromethane slowly to the suspension. Compounds of the formula (XVII) are either known compounds or can be prepared in analogous manner to known compounds. For example, one suitable reaction scheme for the preparation of these compounds is shown below:

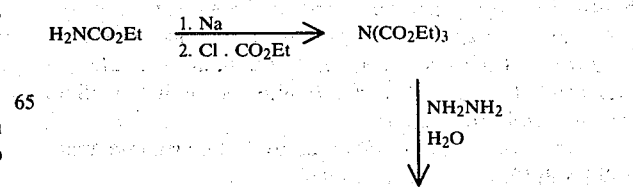

-continued

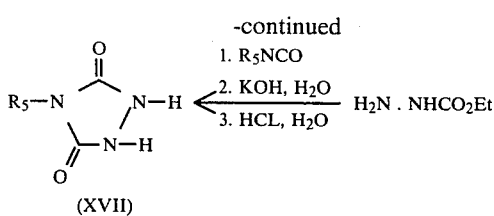

(XVII)

It is believed that compounds of formula (X1) and (1X) wherein L is S are novel compounds, and these compounds are useful intermediates as hereinbefore described. As such, they form an important part of this invention.

It is believed these reactions are best illustrated by use of the following diagram. (The reactions represents by arrows in the diagram are carried out as hereinbefore described, or in an analogous manner).

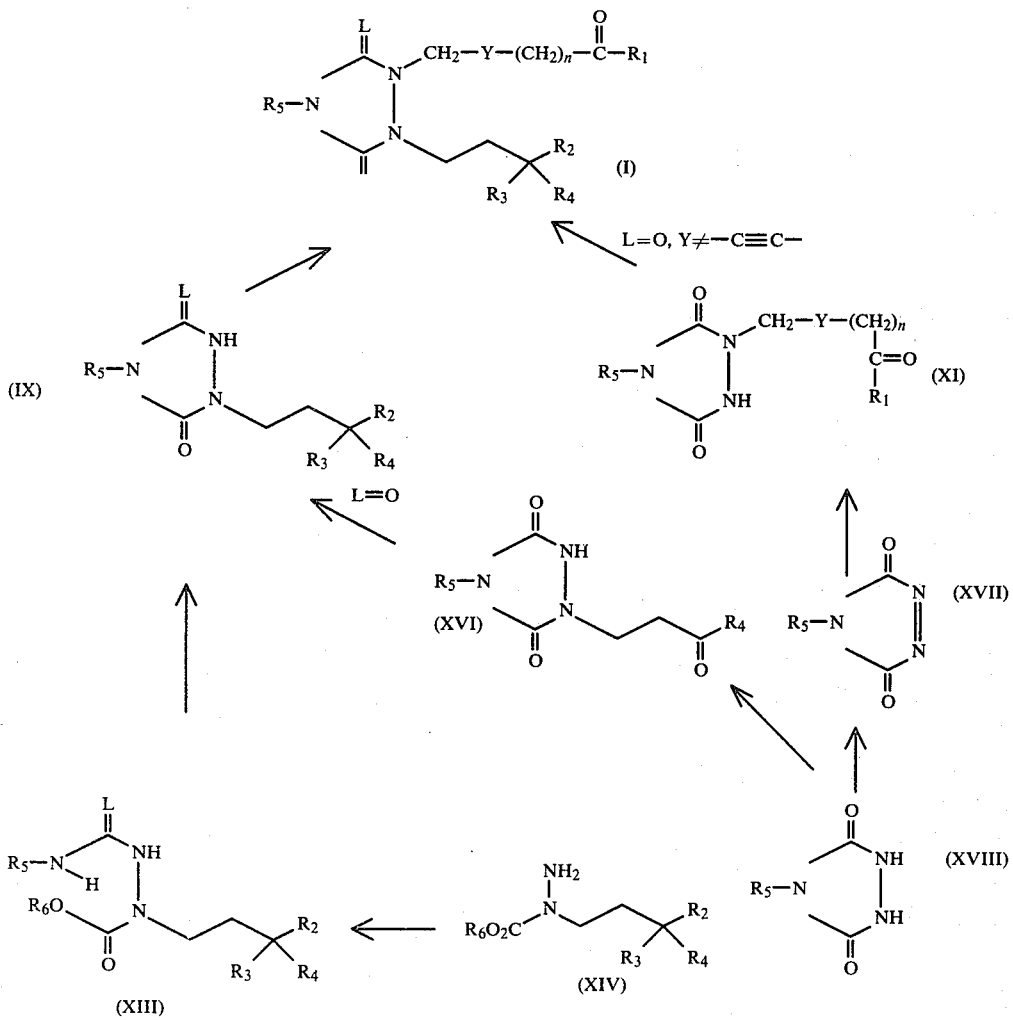

It will of course be realised that the compounds of the formula (I) have an asymmetric centre, and thus are capable of existing in enantiomeric forms. The invention extends to each of these isomeric forms, and to mixtures thereof. The different isomeric forms may be resolved by the usual methods.

Compounds within the formula (I) have useful pharmacological activity. For example compounds within the formula (I) have anti-gastric secretion activity e.g. anti-ulcer activity, cardiovascular activity e.g. anti-hypertensive activity or anti-arrhythmic activity, platelet aggregation inhibition activity, affect the respiratory tract e.g. bronchodilator activity, and have anti-fertility and smooth muscle activity.

In general it may be said that compounds within the formula (I) have a range of pharmacological activities similar to those shown by the natural prostaglandins, but that these activities tend to be rather more selective.

The invention therefore also provides a pharmaceutical composition comprising a compound of the formula (I) and a pharmaceutically acceptable carrier.

Clearly the formulation of the said pharmaceutical composition will depend on the nature of the activity shown by the chosen compound of the formula (I), and on other factors such as preference in a particular area of therapy for a particular mode of administration.

The compositions may be in the form of tablets, capsules, powders, granules, lozenges or liquid preparations, such as oral or sterile parenteral solutions or suspensions.

Tablets and capsules for oral administration may contain conventional excipients such as binding agents, fillers, tabletting lubricants, disintegrants and acceptable wetting agents and the like. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, emulsifying agents, nonaqueous vehicles (which may include edible oils), preservatives, and if desired conventional flavouring or colouring agents, and the like.

For parenteral administration, fluid unit dosage forms may be prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or prophylaxis of disorders in human beings or domestic animals which comprises the administration to the sufferer of an effective amount of a compound of the formula (I).

The following Examples 5 and 15 to 17 illustrate the preparation of the active compounds of the invention. The following Examples 1 to 4 and 6 to 14 illustrate the preparation of intermediates therefor.

Process Variant (b)

EXAMPLE 1

Preparation of non-8-en-2-one

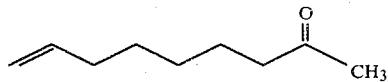

To a solution of 6-bromohex-1-ene (228 g, 0.14 mole) in ethanol was added pentane-2,4-dione (14.8 g, 0.148 mole) and potassium carbonate (20.8 g, 0.15 mole), and the reaction mixture was stirred under reflux for 48 hr. The mixture was cooled, and concentrated in vacuo. The residue was mixed with diethyl ether (400 ml), washed with water (2×200 ml) and saturated sodium chloride solution (200 ml), dried (Na$_2$SO$_4$) and evaporated in vacuo to give an oil (18 g). This oil was distilled to give non-8-en-2-one (8 g), b.pt. 80°–82° C./25 mm Hg.

Oct-7-en-2-one (I.2) was similarly prepared from 5-bromopent-1-ene. B pt. 72°–76° C./30 mm Hg.

EXAMPLE 2

Preparation of 1-(p-toluenesulphonyloxy)-3-methyl-nonan-3-ol

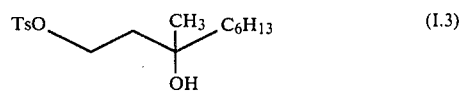

To a slurry of zinc (65.0 g, 1.0 mol) in benzene (100 ml), containing a small crystal of iodine, refluxed with stirring, was added carefully 60 ml of mixture of octan-2-one (76.8 g, 0.6 mol), ethyl bromoacetate (167.0 g, 1.0 mol) and benzene (100 ml). After initiation of the reaction, the rest of the reaction mixture was added at such a rate that reflux was maintained. After complete addition of the ketone mixture the resultant reaction mixture was boiled at reflux for a further 1 hr. The mixture was then cooled and poured into ice-cold 20% sulphuric acid (400 ml), and the mixture was extracted with diethyl ether (4×200 ml). The combined extracts were washed with water (200 ml), saturated sodium hydrogen carbonate solution (2×250 ml) and saturated sodium chloride solution until neutral. The extract was then dried (Na$_2$SO$_4$) and filtered and the filtrate was concentrated in vacuo to give an oil. This residual oil was distilled to afford ethyl 3-methyl-3-hydroxynonanoate (70.0 g), b.pt. 88°–90 C./0.07 mm Hg.

To a slurry of lithium aluminium hydride (12.3 g, 0.325 mol) in diethyl ether (300 ml), under nitrogen and cooled in an ice-bath, was added dropwise a solution of ethyl 3-methyl-3-hydroxynonanoate (70.0 g, 0.325 mol) in diethyl ether (300 ml). The resultant mixture was boiled at reflux for 1 hr, then cooled in an ice-bath. Excess lithium aluminium hydride was destroyed by successive dropwise addition of water (12 ml), 10% sodium hydroxide solution (12 ml) and water (36 ml). The reaction mixture was filtered, the filter cake was washed with diethyl ether (2×100 ml) and the filtrate was washed with saturated sodium chloride solution (1×250 ml) and then dried (Na$_2$SO$_4$) and filtered, and the filtrate was concentrated in vacuo to give 3-methyl-3-hydroxynonan-1-ol (55.0 g) as an oil (i.r.(cm$^{-1}$), OH, 3500). 3-Methyl-3-hydroxy-nonan-1-ol (55.0 g, 0.316 m) was dissolved in pyridine (235 ml) and cooled to 0° C. with stirring. p-Toluenesulphonyl chloride (63.5 g, 0.332 mol) was added portionwise and the resultant mixture stirred for 45 minutes at 0° C. The reaction mixture was stored in a refrigerator for 15 hr and then poured into iced-water (200 ml). The reaction mixture was extracted with diethyl ether (3×200 ml), and the combined extracts were washed with 10% hydrochloric acid (2×200 ml), and saturated sodium chloride solution (3×200 ml) and then dried (Na$_2$SO$_4$). This mixture was filtered, and the filtrate was concentrated at room temperature in vacuo to leave a gum (100 g). This gum was mixed with petrol (b.pt. 60°–80° C., 400 ml) and gradually cooled to −78° C. with stirring, and the petrol was decanted. Residual petrol was removed by evaporation in vacuo at room temperature to give 1-(p-toluenesulphonyloxy)-3-methylnonan-3-ol (90.0 g) as a gum.

Analysis: C, 62.39; H, 8.89; S, 9.27% C$_{17}$H$_{28}$SO$_4$ requires C, 62.18; H, 8.59; S, 9.76%.

I.r (cm$^{-1}$): 3550, OH;

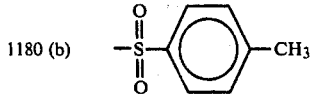

1180 (b)

1-(2′-p-toluene sulphonyl-oxyethyl)cyclohexanol (I.4) was similarly prepared from cyclohexanone.
I.r. (cm$^{-1}$): 3500, OH;

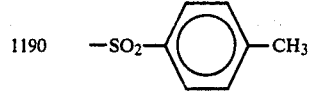

1190

EXAMPLE 3

Preparation of 1-(8′-oxonon-2′-enyl)-4-methyl-1,2,4-triazolidine-3,5-dione

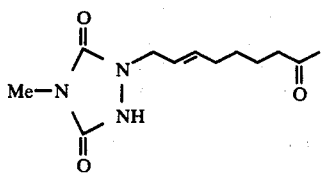

(I.5)

4-Methyl-1,2,4-triazolidine-3,5-dione (4.05 g, 0.035 mol) was suspended with stirring in dichloromethane (100 ml) and cooled to −5° C. Dinitrogen tetroxide (4 ml) in dichloromethane (15 ml) was added dropwise and stirring was continued until a clear, homogeneous, deep red solution was obtained. Sodium sulphate (20 g) was added, and the reaction mixture was stirred for a further 20 minutes and then filtered and evaporated in vacuo at room temperature to give 4-methyl-triazoline-3,5-dione (4.0 g.).

To a solution of the triazolidinedione (4.0 g, 0.035 mol) in benzene (60 ml) at room temperature, under nitrogen was added dropwise a solution of non-8-en-2-one (0.32 mole) in benzene (20 ml), and the resultant solution was refluxed for 1 hr. The solution was concentrated in vacuo, and the residue was chromatographed on silica gel (Merck Kieselgel 60, 100 g) using chloroform as eluant to afford 1-(8′-oxonon-2′-enyl)-4-methyl-1,2,4-triazolidine-3,5-dione as a gum.

N.m.r. (CDCl$_3$), τ: 4.32 m, 2H, C$\underline{H}$=C$\underline{H}$; 5.84 bt, 2H, N—C$\underline{H}_2$—; 6.92 s, 3H, —N—C$\underline{H}_3$; 7.35–8.9 bm, 7.85 s, 11H.

EXAMPLE 4

Preparation of 1-(8′-oxononyl)-4-methyl-1,2,4-triazolidine-3,5-dione

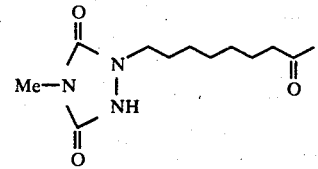

(I.6)

1-(8′-oxonon-2′-enyl)-4-methyl-1,2,4-triazolidine-3,5-dione (0.009 mole) was dissolved in dimethoxyethane (70 ml), 10% palladium on charcoal was added, and the resultant mixture was allowed to take up hydrogen. When the reaction was complete the mixture was filtered, and the filtrate was evaporated in vacuo to yield 1-(8′-oxononyl)-4-methyl-1,2,4-triazolidine-3,5-dione as a gum.

EXAMPLE 5

Preparation of 1-(8-oxononyl)-2-(3″-hydroxy-3″-methylnonyl)-4-methyl-1,2,4-triazolidine-3,5-dione, Compound 1

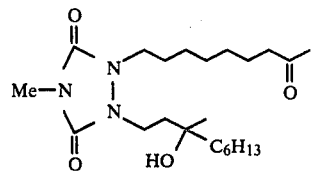

(1)

To a solution of 1-(8′-oxononyl)-4-methyl-1,2,4-triazolidine-3,5-dione (8.4 mole) in hexamethylphosphoramide (35 ml) was added sodium carbonate (24 mole), sodium iodide (9 mole) and 1-(p-toluenesulphonyloxy)-3-methylnonan-3-ol (8.3 mole) in hexamethylphosphoramide (20 ml), and the resultant mixture was stirred at room temperature for 9 days. The mixture was then poured into water (100 ml), acidified with 10% hydrochloric acid and extracted with ethyl acetate (3×150 ml). The combined extracts were washed with water (2×100 ml) and brine (2×100 ml), dried (Na$_2$SO$_4$) and filtered, and the filtrate was evaporated in vacuo. The resultant gum was chromatographed on silica gel (Merck Kieselgel 60, 100 g) using chloroform:methanol as eluant (0–2% methanol) to give 1-(8′-oxononyl)-2-(3″-hydroxy-3″-methylnonyl)-4-methyl-1,2,4-triazolidine-3,5-dione as a gum.

N.m.r. (CDCl$_3$): 6.1–6.8 m, 4H, 2×(C$\underline{H}_2$). 7.0 s, 3H, N—C$\underline{H}_3$; 7.95 d, 3H, CO—C$\underline{H}_3$; 9.6–9.2 m, 31H, (C$\underline{H}_2$)$_{12}$, HO—C—C$\underline{H}_3$, CH$_2$—C$\underline{H}_3$.

I.R (cm$^{-1}$): 3500, OH; 1780 N—C=O; 1680–1740, COCH$_3$, N—C=O.

Mass spec.: meas. mass: 411.3127; calc.mass 411.3097.

The compounds shown in the following Table 1 were prepared in a similar manner, via corresponding intermediates analogous to and prepared in a similar manner (I.5) and (I.6) Examples 3 and 4, and (I.3) and (I.4) of Example 2.

TABLE 1

| Compound | R$_1$ | R$_2$ | R$_4$ | R$_3$ | R$_5$ | Y | n |
|---|---|---|---|---|---|---|---|
| 2 | CH$_3$ | | ⬡ | OH | CH$_3$ | CH=CH | 4 |
| 3 | CH$_3$ | CH$_3$ | C$_6$H$_{13}$ | OH | CH$_3$ | CH$_2$CH$_2$ | 3 |

Compound 2

Mass spectrum: m/e M$^+$ 379.2467 Calc. for C$_{20}$H$_{32}$N$_3$O$_4$ 379.2470.

N.m.r. (CDCl$_3$) τ 4.2–4.7 (m, 2H, C$\underline{H}$=C$\underline{H}$); 5.9–6.0 (brt, 2H, N.C$\underline{H}_2$CH=CH); 6.2–6.4 (m, 2H, NC$\underline{H}_2$); 7.0 (s, 3H, NC$\underline{H}_3$); 7.85 (s, 3H, COC$\underline{H}_3$)

Compound 3

Analysis: Found C, 63.72; H, 10.05; N, 10.40%. $C_{21}H_{39}N_3O_4$ requires C63.45; H 9.89; N 10.57.

Mass spectrum m/e: M+397.2945 Calc. for $C_{21}H_{39}N_3O_4$ 397.2940.

N.m.r. (CDCl$_3$)τ: 6.2–6.6 (brm, 4H, 2 xNC$\underline{H}_2$); 6.95 (s, 3H, NC$\underline{H}_3$); 7–9 (s, 3H, COC$\underline{H}_3$); 8.9 (s, 3H, COHC$\underline{H}_3$); 9.1 (brt, 3H), (CH$_2$)$_5$C$\underline{H}_3$)

I.r. cm$^{-1}$ 3450, OH; 1770 N—C=O; 1680–1730, COCH$_3$N—C=O Process Variant (a)

EXAMPLE 6

Preparation of 3-hydroxy-3,4-dimethylactanonitrile

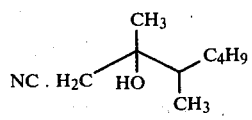
(I.7)

To a stirred solution of sodamide (29.9 g; 0.76 mole) in liquid ammonia (500 ml) was added acetonitrile (36.5 ml; 0.70 mole) in diethyl ether (20 ml) over 1 hr. After stirring for 45 min. 3-methylheptan-2-one (67 g; 0.52 mole) was added dropwise over 1 hr, and stirring was continued for 3 hr. Solid ammonium chloride (43 g) was carefully added, and the mixture was allowed to evaporate overnight. The mixture was partitioned between diethyl ether (800 ml) and water (800 ml), and the organic layer washed with water (2×250 ml), and brine (1×250 ml) and dried (Na$_2$SO$_4$). Evaporation in vacuo gave a yellow oil (75 g).

Fractional distillation gave pure 3-hydroxy-3, 4-dimethylactanonitrile (42.4 g) B.p., 136°–138 ° at 10 mm. Hg.

N.m.r. (CDCl$_3$)τ: 7.06 (s, 1H ex D$_2$O, $\underline{H}$—O), 7.45 (s, 2H, NC.C$\underline{H}_2$); 8.20–8.90 (m, 7H, chain); 8.72 (s, 3H, C$\underline{H}_3$+O); 8.95-9.20 (m, 6H, C$\underline{H}_3$+H and terminal C$\underline{H}_3$—).

I.r. cm$^{-1}$: 3450 —O—H; 2240 —C≡N.

EXAMPLE 7

Preparation of 3-hydroxy-3,4-dimethyloctylamine

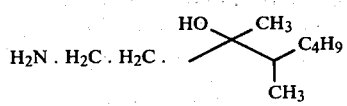
(I.8)

To a stirred suspension of lithium aluminium hydride (10.49 g; 0.28 mole) in dry diethyl ether (200 ml), at 0° C., under nitrogen, was added 3-hydroxy-3,4-dimethylactanonitrile (42 g; 0.24 mole) in dry diethyl ether (100 ml) over 90 min. The suspension was heated under reflux for 1½ hr. and then allowed to cool to room temperature. The excess of hydride was destroyed (10 ml water+10 ml 10% aqueous NaOH solution+30 ml water) and the mixture filtered through kieselguhr with diethyl ether (400 ml) and water (400 ml). The organic layer was washed with water (1×400 ml) and brine (1×250 ml), and dried (Na$_2$SO$_4$) and evaporated to dryness. Fractional distillation gave 3-hydroxy-3,4-dimethyloctylamine as a colourless oil (27 g).

B.pt., 105°–106° at 0.4 mm Hg.

N.m.r. (CDCl$_3$)τ: 7.03 (t, 2H, N—C$\underline{H}_2$), 7.00–760 (s, 3H, ex D$_2$O; N$\underline{H}_2$+O$\underline{H}$) 8.43 (t, 2H, C$\underline{H}_2$), 8.40–9.25 (m, 6H, —(C$\underline{H}_2$)$_3$—), 8.92 (s, 3H, tertiary C$\underline{H}_3$); 9.08 (m, 6H, 2×C$\underline{H}_3$).

I.r., cm$^{-1}$: 3360, 3270 —OH and —NH$_2$; 2950 C—H.

EXAMPLE 8

Preparation of ethyl N-(3'-hydroxy-3',4'-dimethyloctyl) carbamate

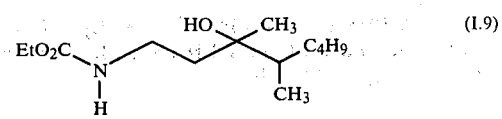
(I.9)

To a stirred suspension of 3-hydroxy-3,4-dimethyoctylamine (4.91 g; 28.38 mmole) and anhydrous sodium carbonate (5 g) in dry etanol (40 ml) was added ethyl chloroformate (3.65 g; 33.6 mmole) in dry ethanol (25 ml), over 30 min. The mixture was heated under reflux for 1 hr and then poured into water (200 ml). The product was extracted into diethyl ether (3×100 ml), and the combined organic layers washed with dilute hydrochloric acid (1×100 ml) and brine (1×100 ml) and dried. (Na$_2$SO$_4$). Evaporation in vacuo gave ethyl N-[3-hydroxy-3,4-dimethyloctyl]-carbamate (6.2 g; 891).

N.m.r. (CDCl$_3$)τ: 4.55 (s, 1H, N—$\underline{H}$); 5.90 (q, 2H, CO$_2$C$\underline{H}_2$); 6.66 (2H, m, N—C$\underline{H}_2$), 7.72 (s, 1H, ex D$_2$O, O—$\underline{H}$), 8.15-9.20 (m, 21H, C$_9$$\underline{H}_{18}$ chain +CO$_2$CH$_2$.C$\underline{H}_3$).

I.r. (cm$^{-1}$): 3340 NH and OH; 1690 and 1520 EtO$_2$C—NH.

EXAMPLE 9

Preparation of Ethyl N-Amino-N-(3'-Hydroxy-3',4'-Dimethyloctyl)-Carbamate

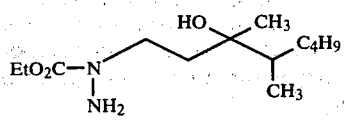
(I.10)

Ethyl N-(3'-hydroxy-3',4'-dimethyloctyl)carbamate (6 g; 24.48 mmole) in diethyl ether (15 ml) was stirred with a solution of sodium nitrite (12 g) in water (8 ml) and cooled to 0° C. A solution of mixture of ice (10 g) and conc. nitric acid (10 ml) was added dropwise to the rapidly stirred mixture over 2 hr. and the resultant blue solution poured into water (250 ml). Extraction with diethyl ether (3×100 ml) removed the product and the combined organic layers were washed with water (100 ml), 5% aqueous sodium bicarbonate solution (100 ml) and brine (100 ml) and dried (Na$_2$SO$_4$). Evaporation in vacuo gave an or ange oil (6.7 g) I.r. (cm$^{-1}$): 1630 and 1510, N—N=O.

To a stirred suspension of AR zinc powder (8 g), sodium acetate (4 g) in glacial acetic acid (25 ml) containing 5 drops of acetic anhydride was added dropwise the nitrosamine product obtained (6.7 g) above in diethyl ether (10 ml). Stirring was continued for 16 hr. at 25° C., and the mixture was filtered through kieselguhr with ether (100 ml) and water (250 ml). The organic layer was washed with water (100 ml) and then poured into 5% aqueous bicarbonate solution (250 ml). The neutral organic layer was washed with 5% aqueous bicarbonate solution (100 ml) and brine (100 ml) and dried over Na$_2$SO$_4$. Evaporation in vacuo gave a colourless oil (6 gm) which was chromatographed in Kieselgel 60 (100 g) in chloroform. Combination of appropriate fractions gave pure ethyl N-amino-N-(3'-hydroxy-3',4'-dimethyloctyl)carbamate (2.50 g).

Mass spectrum m/e: M+260.2108, for $C_{13}H_{28}N_2O_3$ requires 260.2098 ;260 (m*,8) 227 (5), 157 (100) and 111 (54).

N.m.r. (CDCl$_3$)τ: 5.65–6.05 (q, 2H, C$\underline{H}_2O_2C$); 6.15–5.70 (t, 2H, N—C$\underline{H}_2$), 5.90 (s, 3H, ex D$_2$O, N$\underline{H}_2$ and O$\underline{H}$), 8.00–9.30 (m, 21H, C$_9$H$_{18}$ chain and C$\underline{H}_3$CH$_2$.O$_2$C).

I.r. cm$^{-1}$: 3450, 3300, and 3200 O—H and NH$_2$; 1680 EtO$_2$C—N.

Ethyl N-amino-N-(3'-hydroxy-3'-methylnonyl) carbamate (I.11) was prepared in a similar manner from octan-2-one.

N.m.r. (CDCl$_3$): 5.82 (q, 2H, H$_2$C.O$_2$C); 6.05–6.60 (m, 4H, N$\underline{H}_2$ and N-CH$_2$), 8.00–8.95 (15H, m, chain protons), 9.10 (m, 3H, C$\underline{H}_3$).

EXAMPLE 10

Preparation of 2-(3'-Hydroxy-3',4'-dimethyloctyl)-4-Methyl-1,2,4-Triazolidine-3,5-Dione

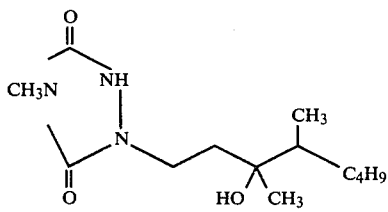

(I.12)

Ethyl N-amino-N-(3'-hydroxy-3',4'-dimethyloctyl-carbamate (2.50 g; 9.62 mmole) and methyl isocyanate (852 mg; 14.9 mmole) in dry toluene (25 ml) were heated under reflux for 2 hr. After cooling to 0° C., with stirring, potassium t-butoxide (2 g. 17.9 mmole) was added and the mixture stirred at room temperature for 16 hr. The mixture was partitioned between water (100 ml) and ethyl acetate (100 ml) and acidified with 5 N HCl. The organic layer was washed with water (2×100 ml) and brine (100 ml) and dried (Na$_2$SO$_4$). Evaporation gave a yellow gum (2.8 g) and chromatography on Kieselgel 60 (25 g) in chloroform gave 2-(3'-hydroxy-3',4'-dimethyloctyl)-4-methyl-1,2,4-triazolidine-3,5-dione as a colourless gum (1.99 g; 76%)

Mass spectrum m/e: M+271.1882, calc. for $C_{13}H_{25}N_3O_3$ 271.1894. 271 (m+,2), 253 (73), 186 (80), 168 (100) and 138(59).

N.m.r. (CDCl$_3$)τ: 6.05–6.45 (t, 2H, N—C$\underline{H}_2$); 6.95 (s, 3H N-C$\underline{H}_3$), 8.00–9.25 (m, 19H, chain).

I.r. (cm$^{-1}$): 3440 OH; 1760 and 1680–1740 N—C=O.

2-(3'-Hydroxy-3'-methylnonyl)-4-methyl-1,2,4-triazolidine-3,5-dione (I. 13) was prepared in an analogous manner from ethyl-N-amino N-(3'-hydroxy-3-methylnonyl)carbamate and methyl isocyanate.

Mass spectrum m/e: M+271.1903, Calc. for $C_{13}H_{25}N_3O_3$ 271.1896.

N.m.r. (CDCl$_3$)τ: 3.70 (1H, br, N—$\underline{H}$); 6.28 (m, 3H, N—CH$_2$ and $\underline{H}$O); 6.96 (s, 3H, N—C$\underline{H}_3$); 7.90–8.93 (m, 15H, C$_7\underline{H}_{15}$ chain), 9.12 (m, 3H, C$\underline{H}_3$).

EXAMPLE 11

Preparation of 2-(3'-Hydroxy-3'-Methylnonyl)-4-Methyl-1,2,4-Triazolidine-3-One-5-Thione

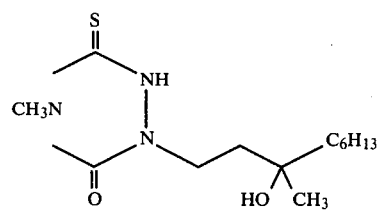

(I.14)

A solution of ethyl N-amino-N-(3'-hydroxy-3-methylnonyl)carbamate (1.812 g; 6.97 mmole), and methyl isothiocyanate (764 mg; 10.5 mmole) in dry toluene (25 ml) was heated under refulx for 2 hrs and then allowed to cool to room temperature. Potassium t-butoxide (1,56 g; 13.96 mmole) was added and the mixture stirred at 25° for 16 hr. The mixture was portitioned between water (100 ml) and ethyl acetate (100 ml) and acidified with 5 M HCl. The aqueous layer was extracted with ethyl acetate (50 ml) and the combined organic layers washed with water (2×100 ml) and brine (100 ml), dried (Na$_2$SO$_4$), and evaporated to dryness and chromatography of the residue on Kieselgel 60 (10 g) in chloroform gave 2-(3'-hydroxy-3'-methylnonyl)-4-methyl-1,2,4-triazolidine-3-one-5-thione as a gum (1.83 g; 91%).

Mass spectrum m/e: M+287.1652 calc. for $C_{13}H_{25}N_3O_2S$ 287.1620.

N.m.r. (CDCl$_3$)τ: 2.50–3.00 (m, 2H, N$\underline{H}$ and OH), 6.08 (t, 2H, N—C$\underline{H}_2$); 6.72 (s, 3H, N—C$\underline{H}_3$) 8.10–9.23 (m, 18H, chain).

I.r. (cm$^{-1}$): 3500 to 3110 NH and OH; 1760–1680 N—C=O; 1530 and 1465 N—C=S.

EXAMPLE 12

Preparation of 2-(3'-Hydroxyoctyl)-4-Methyl-1,2,4-Triazolidine-3,5-Dione

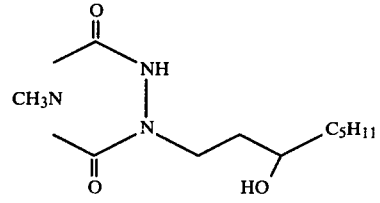

(I.15)

A solution of 4-methyl-1,2,4-triazolidine-3,5-dione (16 g; 0.14 mmole) in dry 1:1 benzene-dimethylformamide (100 ml) was heated under reflux, with stirring under nitrogen, and potassium t-butoxide (17.62 g), was added. The resultant suspension was heated under reflux for 2 hr. and then n-pentyl vinyl ketone (12,568; 0.10 mole) in dry dimethylformamide (10 ml) added dropwise. After 2 days the mixture was allowed to cool to room temperature and partitioned between 5 M HCl (200 ml) and ethyl acetate (100 ml). The aqueous layer was extracted with ethyl acetate (5×70 ml) and the combined organic layers washed with water (2×100 ml) and brine (100 ml) and dried (Na$_2$SO$_4$). Evaporation in vacuo gave an oil. Recrystallisation from ethyl acetate - 60/80 petroleum ether gave 2-(3'-oxo-octyl)-4- methyl-1,2,4-triazolidine-3,5-dione (16.03 g; 66%). m.pt., 75°–76°

N.m.r. (d⁶DMSO)τ: 6.35 (t, 2H, N—C$\underline{H}_2$); 7.10 (s, 3H, N—C$\underline{H}_3$); 7.15–7.80 (m, 4H, H$_2$C.CO.C$\underline{H}_2$); 8.20–8.90 (m, 6H, —(C$\underline{H}_2$)$_3$-chain); 9.12 (m, 3H, C$\underline{H}_3$)

2-(3'-oxooctyl)-4-methyl-1,2,4-triazolidine-3,5-dione (1.934 g; 8.03 mmole) in dry ethanol (50 ml) was stirred at 20° C. and sodium borohydride (330 mg) added over 5 hr. After 1 hr., the excess of borohydride was decomposed with acetic acid and the mixture evaporated to dryness. The residue was partitioned between ethyl acetate (100 ml) and water (100 ml), and the aqueous layer was extracted with ethyl acetate (2×100 ml). The combined organic layers were washed with brine (100 ml), dried (Na$_2$SO$_4$), and evaporation in vacuo gave 2-(3'hydroxyoctyl-4-methyl-1,2,4-triazolidine-3,5-dione as a waxy solid (1.83 g; 94%)

Mass spectrum m/e: M$^+$243.1577 Calc. for C$_{11}$H$_{21}$N$_3$O$_3$ 243.1582.

N.m.r. (d⁶-DMSO)τ: 6.25–6.80 (m, 4H, NC$\underline{H}_2$+N$\underline{H}$+O$\underline{H}$); 7.13 (s, 3H, N—C$\underline{H}_3$) 8.20–8.90 (m, 10H, —(C$\underline{H}_2$)$_5$-chain); 9.13 (m, 3H, C$\underline{H}_3$).

EXAMPLE 13

Preparation of 9-oxodec-2-yn-1-ol

(I.16)

t-Butyl acetoacetate (9.2 g; 58 mmole) was added dropwise to a stirred suspension of sodium hydride (1.75 g; 80% suspension in oil) in dry 1:1 benzene-dimethylformamide (120 ml) under nitrogen, under reflux. After 30 minutes, sodium iodide (2.5 g) was added, followed by dropwise addition of 7-chloro-1-tetrahydropyranyloxy-hept-2-yne (11 g; 47.5 mmole), and the mixture was heated under reflux for 5 hours. The mixture was allowed to cool to room temperature and partitioned between diethyl ether (800 ml) and water (800 ml). The organic layer was washed with water (500 ml) and brine (500 ml), dried (Na$_2$SO$_4$) and evaporated to dryness. Fractional distillation gave the substituted acetoacetate (7.5 g) B.pt 170–174 at 0.4 mm Hg.

The foregoing material in dry toluene (25 ml) was heated under reflux with p-toluenesulphonic acid (400 mg) for 17 hours and allowed to cool to room temperature. The brown solution was diluted with diethyl ether (100 ml), wahed with 5% aqueous sodium bicarbonate solution (100 ml), brine (100 ml) and dried (Na$_2$SO$_4$). Evaporation in vacuo gave a brown oil (6 g) which was stirred with methanol (50 ml) containing 5 M H$_2$SO$_4$ (5 ml) at 20° C. for 18 hours. Work-up as above followed by chromatography on Kieselgel 60 (60 g) in chloroform gave 9-oxodec-2-yn-1-ol as a yellow oil (2.07 g).

N.m.r. (DCDl$_3$)τ: 5.80 (t, 2H, OC$\underline{H}_2$.C≡C); 6.25 (s, 1H, ex D$_2$O, O$\underline{H}$); 7.38–7.75 (m, 4H, 2×C$\underline{H}_2$); 7.86 (s, 3H, C$\underline{H}_3$CO); 8.20–8.75 (m, 6H, —(C$\underline{H}_2$)$_3$—chain). I.r. (cm$^{-1}$): 3405 OH; 2220 C≡C; and 1710 C═O.

EXAMPLE 14

Preparation of 9-bromo-9-oxodec-2-yne

(I.17)

9-Oxodec-2-yl-1-ol (903 mg; 5.38 mmole) and dry triethylamine (1.2 ml) in dry dichloromethane (30 ml) were cooled to −10° C. with stirring, and methanesulphonyl chloride (786 mg; 6.83 mmole) was added dropwise over 15 minutes. After stirring for a further 40 minutes the reaction mixture was washed with ice-cold water (50 ml), 5 M HCl (50 ml), 5% aqueous sodium bicarbonate solution (50 ml) and brine (50 ml) and dried (Na$_2$SO$_4$). Evaporation in vacuo gave the methanesulphonate (1.13 g).

N.m.r. (CDCl$_3$)τ: 5.16 (t, 2H, O.C$\underline{H}_2$.C≡C); 6.90 (s, 3H, C$\underline{H}_3$SO$_3$); 7.88 (s, 3H, C$\underline{H}_3$CO).

The foregoing methanesulphonate (1.13 g) in dry acetone (20 ml) was stirred with anhydrous lithium bromide (2 g) at room temperature for 19 hours. The mixture was concentrated in vacuo and then partitioned between diethyl ether (50 ml) and water (50 ml), and the organic layer was washed with brine (50 ml), and dried (Na$_2$SO$_4$). Evaporation gave 1-bromo-9-oxodec-2-yne as a yellow oil (870 mg; 70%). N.m.r. (CDCl$_3$): 6.04 (t, 2H, BrH$_2$C.C≡C); 7.40–7.90 (m, 4H, 2×C$\underline{H}_2$), 7.88 (s, 3H, C$\underline{H}_3$CO); 8.20–8.75 (m, 6H, —(C$\underline{H}_2$)$_3$—chain). I.r. (cm$^{-1}$): 2220 C≡C; 1710 C═O.

1-Bromo-8-oxonon-2-yne (I.18) was prepared in a similar way from t-butyl acetoacetate and 6-chloro-1-tetra-hydropyranyloxyhex-2-yne by alkylation of the sodium salt in 1:1 dimethylformamide-benzene. Acidic cleavage in methanol-sulphuric acid gave the alcohol which was readily converted into the bromide. N.m.r. (CDCl$_3$)τ: 6.05 (t, 2H, BrH$_2$C.C≡C); 7.45–7.80 (m, 4H, 2×C$\underline{H}_2$); 7.85 (s, 3H, C$\underline{H}_3$CO); 8.00–8.65 (m, 4H, —CH$_2$)$_2$—chain). I.r. (cm$^{-1}$): 2220 C≡C; 1710 CH$_3$C═O; 605 C—Br.

EXAMPLE 15

Preparation of 1-(8'-Oxonon-2'-ynyl)-2-(3''-hydroxy-3'', 4''-dimethyloctyl)-4-methyl-1,2,4-triazolidine-3,5-dione, Compound 4

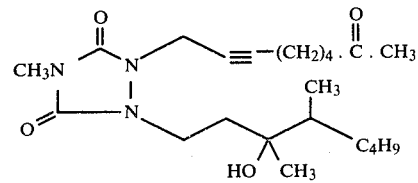

A solution of 2-(3'-hydroxy-3',4'-dimethyloctyl-4-methyl-1,2,4-triazolidine-3,5-dione (720 mg; 2.66 mmole) and 1-bromo-8-oxonon-2-yne (833 mg; 3.83 mmole) in dry dimethylformamide (25 ml) was stirred with anhydrous lithium carbonate (316 mg; 4.26 mmole) at 20° C. for 2 days. The mixture was partitioned between ethyl acetate (100 ml) and water (100 ml) and acidified with 5 M HCl. The organic layer was washed with water (100 ml) and brine (100 ml), dried (Na$_2$SO$_4$) and evaporated to dryness. The residue was chromatographed on Kieselgel 60 (30 g) in chloroform and combination of the appropriate fractions gave 1-(8'-oxonon-2-ynyl)-2-(3''-hydroxy-3'',4''-dimethyloctyl)-4-methyl-1,2,4-triazolidine-3,5-dione as a gum (906 mg; 84%). Mass spectrum m/e: M$^+$ 407.2786 calculated for C$_{22}$H$_{37}$N$_3$O$_4$ 407.2784. N.m.r.τ: 5.71 (t, 2H, N—C$\underline{H}_2$.C≡C), 6.00–6.45 (m. 2H, N—C$\underline{H}_2$); 6.94 (s, 3H, N—C$\underline{H}_3$); 7.40–800 (m,4H, 2×C$\underline{H}_2$); 7.88 (s, 3H, C$\underline{H}_3$CO); 8.05–9.25 (m, 22H, —(C$\underline{H}_2$)$_2$— and C$_9\underline{H}_{18}$ chain). I.R. (cm$^{-1}$): 3460 OH; 2220 —C≡C—; 1775 and 1770–1680 N—C=O; 1700 C=O.

EXAMPLE 16

Preparation of 1-(8′-oxonon-2-enyl)-2-(3″-hydroxy-3″,4″-dimethyloctyl)-4-methyl-1,2,4-triazolidine-3,5-dione, Compound 5

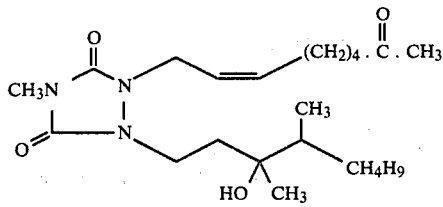

1-(8′-Oxonon-2-ynyl)-2-(3″-hydroxy-3″,4″-dimethyloctyl)-4-methyl-1,2,4-triazolidine-3,5-dione (507 mg; 1.25 mmole) in ethanol (35 ml) containing quinoline (5 ml) was hydrogenated over 5% palladium supported on calcium carbonate (61 mg) until uptake ceased. The mixture was filtered and the filtrate evaporated in vacuo. The residue was taken up in ethyl acetate (50 ml) and wahed with 5 M HCl (25 ml), water (25 ml), brine (25 ml) and dried (Na$_2$SO$_4$). Evaporation in vacuo gave a gum (625 mg) which on chromatography on Kieselgel 60 (15 g) in chloroform gave 1-(8′-oxonon-2-enyl)-2-(3″-hydroxy-3″,4″-dimethyloctyl)-4-methyl-1,2,4-triazolidine-3,5-dione as a gum (296 mg). Mass spectrum m/e: M$^+$ 409.2949 calculated for C$_{22}$H$_{39}$N$_3$O$_4$ 409.2940.

N.m.r. (CDCl$_3$): 4.25–4.80 (m, 2H, C$\underline{H}$=C$\underline{H}$); 5.77 (d, 2H, N—C$\underline{H_2}$C=C); 6.05–6.50 (m, 2H, N—C$\underline{H_2}$); 6.94 (s, 3H, N—C$\underline{H_3}$); 7.45–7.80 (m, 4H, 2×C$\underline{H_2}$); 7.87 (s, 3H, C$\underline{H_3}$CO); 8.05–9.30 (m, 22H, —(CH$_2$)$_2$—and C$_9$H$_{18}$ chain. I.r. (cm$^{-1}$) 3450 OH; 1770 and 1770–1680 N—C=O; 1700 C=O; 1595 (w) C=C.

EXAMPLE 17

Preparation of 1-(9′-oxodecyl)-2-(3″-hydroxy-3″,4″-dimethyloctyl)-4-methyl-1,2,4-triazolidine-3,5-dione, Compound 6

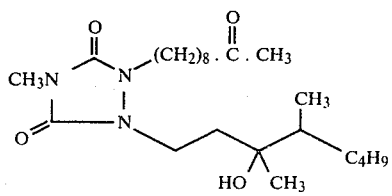

2-(3″-Hydroxy-3′,4′-dimethyloctyl)-4-methyl-1,2,4-triazolidine-3,5-dione (1.167 g; 4.31 mmole) and 1-bromo-9-oxodec-2-yne (1.039 g; 4.5 mmole) in dry dimethylformamide (35 ml) were stirred at 20° C. with anhydrous lithium carbonate (548 mg; 7.40 mmole) for 4 days. The mixture was partitioned between water (100 ml) and ethyl acetate (100 ml) and acidified with 5 M HCl. The organic layer was washed with water (100 ml) and brine (100 ml), dried (Na$_2$SO$_4$), and evaporated in vacuo. The residue was chromatographed on Kieselgel 60 (15 g) in chloroform and gave 1-(9′-oxodec-2′-ynyl)-2-(3″-hydroxy-3″,4″-dimethyloctyl)-4-methyl-1,2,4-triazolidine-3,5-dione as a gum (965 mg; 541). Mass spectrum m/e: M$^+$: 421.2937, calculated for C$_{23}$H$_{39}$N$_3$O$_4$ 421.2940. N.m.r. (CDCl$_3$): 5.74 (t, 2H, N—CH$_2$—C=C); 6.94 (s, 3H, N—CH$_3$); 7.88 (s, 3H, CH$_3$CO).

A solution of the foregoing triazolidinedione (670 mg; 1.42 mmole) in ethanol (40 ml) was hydrogenated over 10% palladised charcoal (130 mg) until uptake ceased. The catalyst was removed by filtration, and evaporation of the filtrate in vacuo gave 1-(9′-oxodecyl)-2-(3″-hydroxy-3″,4″-dimethyl)-4-methyl-1,2,4-triazolidine-3,5-dione as a gum (644 mg). Mass spectrum m/e M$^+$ 425.3230 calculated for C$_{23}$H$_{43}$N$_3$O$_4$ 425.3253.

The compounds shown in the following Table 2 were similarly prepared, via corresponding intermediates analogous to and prepared in a similar manner to (I.16) of Example 13 and (I.12) to (I.14) of Examples 10 and 11.

Reduction to Compound 7 was carried out with palladium on calcium carbonate in place of on charcoal.

TABLE 2

$$\text{structure with } R_5\text{-N, N-CH}_2\text{-Y-(CH}_2)_n\text{-C(=O)-R}_1, \text{ Z, and } R_2, R_3, R_4$$

| Compound | R$_1$ | R$_2$ | R$_4$ | R$_3$ | R$_5$ | Y | Z | n |
|---|---|---|---|---|---|---|---|---|
| 7 | CH$_3$ | CH$_3$ | —⌬—F | OH | CH$_3$ | —CH=CH— | O | 4 |
| 8 | CH$_3$ | H | C$_5$H$_{11}$ | OH | CH$_3$ | —CH$_2$CH$_2$ | O | 4 |
| 9 | CH$_3$ | CH$_3$ | C$_6$H$_{13}$ | OH | CH$_3$ | —CH$_2$CH$_2$— | O | 5 | 4 |

Compound 7

Mass spectrum m/e: M$^+$ 419.2203 Calculated for C$_{22}$H$_{30}$N$_3$O$_4$F 419.2220.

N.m.r. (CDCl$_3$)τ: 2.30–3.20 (m, 4H, aromatic); 4.25–4.80 (m, 2H, C$\underline{H}$=C$\underline{H}$); 7.02 (s, 3H, N—C$\underline{H_3}$); 7.87 (s, 3H, C$\underline{H_3}$CO); 7.30–8.80 (m, 13H, (C$\underline{H_2}$)$_4$ chain +C$\underline{H_2}$+C$\underline{H_3}$).

I.r. (cm$^{-1}$): 3440. OH; 1765–1680 N—C=O; 1710 CO; 1600 C=C.

Compound 8

Mass spectrum m/e: M$^+$ 383.2772 Calculated for C$_{22}$H$_{37}$N$_3$O$_4$ 383.2784.

Analysis: Found C, 63.02; H 9.91; N 10.31% C$_{20}$H$_{37}$N$_3$O$_4$ requires C, 62.63; H, 9.72; N, 10.96%.

N.m.r. (CDCl$_3$)τ: 6.10–6.70 (m, 6H, 2×CH$_2$+CHOH); 6.98 (s, 3H, N—CH$_3$); 7.35–7.75 (t, 2H, CH$_2$CO); 7.91 (s, 3H, COCH$_3$); 8.00–8.90 (m, 20H, (CH$_2$)$_5$ and (CH$_2$)$_5$ chains); 9.12 (m, 3H, CH$_3$).

I.r. (cm$^{-1}$): 3450 OH; 1765 N—C=O; 1770–1680 N—C=O; 1700 C=O.

Compound 9

Mass spectrum m/e: M+ 427.2843 Calculated for $C_{22}H_{41}N_3O_3S$ 427.2868.

N.m.r. (CDCl$_3$); 5.75–6.22 (t, 2H, N—C$\underline{H}_2$); 6.50–7.10 (m, 3H, N—C$\underline{H}_2$+OH); 6.80 (s, 3H, N—C$\underline{H}_3$); 7.40–7.73 (t, 2H, C$\underline{H}_2$CO); 7.87 (s, 3H, COC$\underline{H}_3$); 8.00–9.:00 (m, 25H, (C$\underline{H}_2$)$_5$ and C$_7\underline{H}_{15}$ chains); 9.12 (m, 3H, C$\underline{H}_3$).

I.r. (cm$^{-1}$): 3500 OH; 1700 N—C=O and C=O 1430 N—C=S.

PHARMACOLOGICAL DATA

Bronchodilation activity

1. The compounds were examined for their ability to inhibit 5-hydroxytryptamine or histamine induced bronchoconstriction in the anaesthetised, artificially respired guinea pig (Konzett-Rössler preparation). The compounds were administered intravenously.

2. The compounds were also examined for their ability to protect conscious guinea pigs against bronchoconstriction induced by an histamine aerosol (Herxheimer test). In these experiments the compounds were administered by aerosol. The results are the mean of several experiments.

Both sets of test results are shown in Table A.

TABLE A

| Compound No | Konzett-Rossler ED$_{50}$ μg/kg i.v. | Herxheimer % increase in preconvulsive coughing time at 10 μg/ml after two minutes. |
|---|---|---|
| 1 | 2.7 | Active |
| 8 | 6.9 | 31 |
| 9 | 26.5 | 52 |

Toxicity

No toxic effects were observed in these tests.

What we claim is:

1. A compound of the formula:

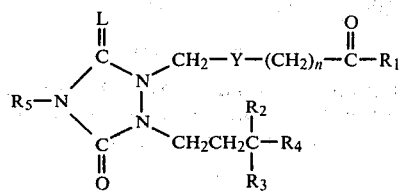

and salts thereof wherein
n is 4;
Y is —CH$_2$CH$_2$—;
L is O or S:
R$_1$ is alkyl of from 1 to 4 carbon atoms;
R$_2$ is hydrogen or alkyl of 1 to 4 carbon atoms;
R$_3$ is hydroxy;
R$_4$ is alkyl of 1 to 9 carbon atoms; and
R$_5$ is alkyl of 1 to 6 carbon atoms.

2. A compound according to claim 1 of the formula:

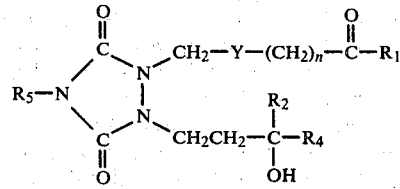

wherein
Y, n, R$_1$, and R$_4$ and R$_5$ are as therein defined; and R$_2$ is hydrogen, methyl, or ethyl.

3. A compound according to claim 2 wherein R$_4$ is alkyl of 4 to 9 carbon atoms; and R$_5$ is methyl.

4. A compound according to claim 2 wherein R$_1$ is methyl.

5. A compound according to claim 2 wherein R$_2$ is hydrogen, methyl or ethyl.

6. A compound according to claim 5 wherein R$_2$ is methyl.

7. A compound according to claim 2 wherein R$_4$ is alkyl of 4 to 9 carbon atoms.

8. A compound according to claim 2 wherein R$_5$ is methyl.

9. A compound according to claim 2 wherein R$_4$ is n-pentyl, n-hexyl or n-heptyl.

10. A compound according to claim 2 wherein R$_4$ is hex-2-yl, hept-2-yl or oct-2-yl.

11. A compound according to claim 3 wherein R$_2$ is methyl.

12. A compound according to claim 3 wherein R$_4$ is n-pentyl, n-hexyl or n-heptyl.

13. A compound according to claim 3 wherein R$_4$ is hex-2-yl, hept-2-yl or oct-2-yl.

14. 1-(8'-oxononyl)-2-(3"-hydroxy-3"-methylnonyl)-4-methyl-1,2,4-triazolidine-3,5-dione.

* * * * *